United States Patent [19]
Moberg

[11] Patent Number: 5,383,473
[45] Date of Patent: Jan. 24, 1995

[54] RATE-RESPONSIVE IMPLANTABLE STIMULATION DEVICE HAVING A MINIATURE HYBRID-MOUNTABLE ACCELEROMETER-BASED SENSOR AND METHOD OF FABRICATION

[75] Inventor: Sheldon B. Moberg, Kagel Canyon, Calif.

[73] Assignee: Pacesetter, Inc., Sylmar, Calif.

[21] Appl. No.: 59,698

[22] Filed: May 10, 1993

[51] Int. Cl.$^6$ .................. G01P 15/09; H01L 41/04
[52] U.S. Cl. ................... 128/782; 310/348; 73/517 AV; 607/2; 607/19
[58] Field of Search ............. 607/2, 9, 19, 36, 17; 128/774, 782, 739, 740, 670; 310/348, 338, 339; 73/517 R, 517 AV

[56] References Cited

U.S. PATENT DOCUMENTS

| | | | |
|---|---|---|---|
| 4,140,132 | 2/1979 | Dahl | 128/419 PG |
| 4,305,396 | 12/1981 | Wittkampf et al. | 128/419 PG |
| 4,428,378 | 1/1984 | Anderson et al. | 128/419 PG |
| 4,443,730 | 4/1984 | Kitamura et al. | 310/330 |
| 4,686,988 | 8/1987 | Sholder | 128/419 PT |
| 4,712,555 | 12/1987 | Thornander et al. | 128/419 pg |
| 4,786,837 | 11/1988 | Kalnin et al. | 310/330 |
| 4,791,931 | 12/1988 | Slate | 128/419 PG |
| 4,860,751 | 8/1989 | Callaghan | 607/020 |
| 4,896,068 | 1/1990 | Nilsson | 310/330 |
| 4,922,930 | 5/1990 | Adkins et al. | 607/19 |
| 5,014,700 | 5/1991 | Alt | 128/419 PG |
| 5,027,657 | 7/1991 | Juckenack et al. | 73/517 R |
| 5,031,615 | 7/1991 | Alt | 128/419 PG |
| 5,040,534 | 8/1991 | Mann et al. | 128/419 PG |
| 5,040,535 | 8/1991 | Mann et al. | 128/419 PG |
| 5,044,366 | 9/1991 | Alt | 128/419 PG |
| 5,128,581 | 7/1992 | Nakayama et al. | 73/517 R |

OTHER PUBLICATIONS

Atochem Sensors, Inc. Product Brochure, *Standard and Custom Piezo film components*, pp. 1–10 (1991).
Bacharach, David W. et al., "Activity-Base Pacing: Comparison of a Device Using an Accelerometer Versus a Piezoelectric Crystal," *Pace*, vol. 15, pp. 188–196 (Feb. 1992).
Piezo Electric Products, Inc., "Piezoceramic Design Notes," *Sensors* Mar. (1984).
Salerno, David M. et al., "Seismocardiography: A New Technique for Recording Cardiac Vibrations. Concept, Method, and Initial Observations," *Journal of Cardiovascular Technology*, vol. 9, No. 2, 1990, pp. 111–118.
Salerno, David M. et al., "Seismocardiography for Monitoring Changes in Left Ventricular Function During Ischemia," *Chest*, vol. 100, pp. 991–993 (Oct. 1991).
Salerno, David M. et al., "Seismocardiographic Changes Associated With Obstruction of Coronary Blood Flow During Balloon Angioplasty," *The American Journal of Cardiology*, vol. 68, pp. 201–207 (Jul. 15, 1991).
Sandler, H. et al., "Miniature Implantable Accelerometers," pp.165–174.

*Primary Examiner*—William E. Kamm
*Assistant Examiner*—Kennedy J. Schaetzle
*Attorney, Agent, or Firm*—Lisa P. Weinberg; Malcolm J. Romano

[57] ABSTRACT

A miniature, hybrid-mountable, accelerometer-based, physical activity sensor for use with a rate-responsive implantable stimulation device is provided. The physical activity sensor is constructed as a cantilever beam having a film of a piezoelectric polymer adhered to each surface of an electrically conductive substrate. The piezoelectric films are highly resistant to fracturing during manufacture and in use, and they provide a strong output signal when stressed in response to bodily accelerations. A pair of electrically conductive supports serve to anchor the physical activity sensor to a substrate and deliver the output signal provided by the sensor to circuitry within the rate-responsive implantable stimulation device. The physical activity sensor is adapted to be mounted directly to conductive traces on a suitable substrate, preferably an implantable stimulation device hybrid.

24 Claims, 5 Drawing Sheets

RATE-RESPONSIVE IMPLANTABLE STIMULATION DEVICE HAVING A MINIATURE HYBRID-MOUNTABLE ACCELEROMETER-BASED SENSOR AND METHOD OF FABRICATION

BACKGROUND OF THE INVENTION

This invention relates to cardiac stimulating devices and particularly to implantable cardiac stimulating devices capable of providing rate-responsive pacing therapy. More particularly, this invention is directed toward a miniature, accelerometer-based, physical activity sensor particularly adapted to be mounted within such devices, for measuring levels to which a patient is engaged in physical activity, so that rate-responsive pacing therapy may be administered accordingly.

A pacemaker is a type of implantable medical device which delivers electrical stimulation pulses to cardiac tissue to relieve symptoms associated with bradycardia—a condition in which a patient cannot normally maintain a physiologically acceptable heart rate. Early pacemakers delivered stimulation pulses at regular intervals in order to maintain a predetermined heart rate, which was typically set at a rate deemed to be appropriate for the patient at rest. The predetermined rate was usually set at the time the pacemaker was implanted, and in more advanced pacemakers, could be set remotely after implantation.

Early advances in pacemaker technology included the ability to sense intrinsic cardiac activity of a patient (i.e., the intercardiac electrogram, or "IEGM"), which led to the development of "demand pacemakers," so named because stimulation pulses were provided only as needed by the heart. Demand pacemakers are capable of detecting a spontaneous, hemodynamically effective, cardiac contraction which occurs within a predetermined time period (commonly referred to as the "escape interval") following a preceding contraction. When a naturally occurring contraction is detected within the escape interval, a demand pacemaker does not deliver a pacing pulse. The ability of demand pacemakers to avoid delivery of unnecessary stimulation pulses is desirable, because it extends battery life.

Early demand pacemakers enabled a physician to adjust the heart rate to be maintained by telemetrically adjusting the length of the escape interval. However, this flexibility only allowed for adjustments to a fixed "programmed rate," and did not accommodate patients who required increased or decreased heart rates to meet changing physiological requirements during periods of elevated or reduced physical activity. Therefore, unlike a person with a properly functioning heart, these patients were paced so that a constant heart rate was maintained regardless of the level to which the patient was engaged in physical activity. Thus, during periods of elevated physical activity, these patients were subject to adverse physiological consequences, including lightheadedness and episodes of fainting, because their heart rates were forced by the pacemaker to remain constant.

Later pacemakers were capable of adjusting the rate at which pacing pulses are delivered in accordance with metabolic needs of the patient. These devices, known as "rate-responsive pacemakers," typically maintain a predetermined minimum heart rate when the patient is engaged in physical activity at or below a threshold level, and gradually increase the maintained heart rate in accordance with increases in physical activity until a maximum rate is reached. Rate-responsive pacemakers typically include circuitry that correlates measured physical activity to a desirable heart rate. In many rate-responsive pacemakers, the minimum heart rate, maximum heart rate, and the slope or curve between the minimum heart rate and the maximum heart rate are telemetrically programmable to meet the needs of a particular patient.

One approach that has been considered for correlating physical activity to an appropriate heart rate involves measuring a physiological parameter that reflects the level to which the patient is engaged in physical activity. Physiological parameters that have been considered include central venous blood temperature, blood pH level, QT time interval and respiration rate. However, certain drawbacks such as slow response time, excessive emotionally induced variations, and wide variability across individuals, render the use of certain physiological parameters difficult, and accordingly, they have not been widely applied in practice.

More generally accepted have been rate-responsive pacemakers which employ sensors that transduce mechanical forces associated with physical activity. A widely used type of sensor incorporates a piezoelectric crystal which generates a measurable electrical potential when a mechanical stress resulting from physical activity is applied to the sensor. U.S. Pat. No. 4,140,132 (to Dahl) and U.S. Pat. No. 4,428,378 (to Anderson et al.) describe examples of rate-responsive pacemakers that maintain a paced heart rate in accordance with physical activity as measured by a piezoelectric sensor.

Despite the widespread use of piezoelectric sensors in rate-responsive pacemakers for measuring physical activity, certain difficulties remain which have yet to be overcome. For example, sensors that employ piezoelectric crystals typically provide extremely small output signals, and subsequent signal processing is often difficult. The small output signals provided by these sensors are usually the result of design choices which are made to compensate for the fragility of the crystals. More precisely, piezoelectric crystals are known to be extremely brittle and subject to fracturing if excessively stressed. To prevent fracturing while in use, sensors must be designed so that relatively high levels of physical exertion by patients do not cause stresses that are beyond the tolerance limits of the crystals. However, the output signals provided by piezoelectric sensors are directly proportional to the magnitude of the mechanical stresses experienced by the piezoelectric material. Thus, to ensure that these known sensors function properly over the lifetime of the pacemaker, the strength of the output signals provided by many of these devices is sacrificed to some extent.

The fragility of piezoelectric crystals also presents certain difficulties during the fabrication process. First, the process of assembling a sensor incorporating a piezoelectric crystal is difficult because handling of the piezoelectric crystal during sensor assembly can cause stresses which exceed the tolerance limits of the crystal. Also, the process of securing the sensor to a suitable supporting structure in the pacemaker can cause unacceptably high stresses. Thus, the fabrication process for pacemakers which incorporate physical activity sensors that rely on piezoelectric crystals may require more expensive equipment and time-consuming procedures than would otherwise be desirable.

Piezoelectric sensors that are constructed in the form of a weighted cantilever beam, such as the sensor described in U.S. Pat. No. 4,140,132 (to Dahl), present further difficulties during the fabrication process. Typically, these sensors are not free-standing; therefore, unless they are secured to a suitable supporting structure, they may tip over. The impact of a sensor on a rigid material can cause the sensor to experience a stress of significant magnitude and as described above, a fracture may result. During the fabrication of a pacemaker, the sensor is usually adhered to a supporting structure with a suitable epoxy. However, the epoxy usually cures very slowly, so the possibility of tipping and subsequent breakage is great, unless additional precautions, such as the insertion of a shim, are used to restrain the cantilever beam from tipping until the epoxy has cured. Of course, the use of additional precautions is undesirable, since they add complexity to the fabrication process.

Another concern regarding piezoelectric physical activity sensors relates to the size and number of components required to construct the sensors. There is tremendous demand for implantable cardiac stimulating devices of reduced size but increased functionality. Many piezoelectric physical activity sensors, especially those of a cantilever beam design, require supporting members for anchoring the sensor to a suitable substrate, as well as a pair of electrical contacts for conducting an output signal provided by the sensor to circuitry within the pacemaker. It is often difficult to accommodate these components within the confines of a pacemaker of acceptable size, and accordingly, it would be desirable to reduce to the greatest extent possible the size and number of components necessary to implement a physical activity sensor.

What is needed therefore is an improved physical activity sensor suitable for use with a rate-responsive pacemaker that overcomes the deficiencies associated with the prior art sensors described above. The improved sensor should provide a relatively strong output signal and should be manufacturable in an efficient and cost-effective manner. Ideally, the 10 sensor should be easy to secure to a substrate in the pacemaker. More particularly, the sensor should be mountable to the pacemaker hybrid, so that the assembly and installation of the sensor can be conveniently integrated to the hybrid manufacturing process. The sensor should also be resistant to breakage, both during fabrication and in use. Finally, the sensor should be compact, both in terms of its overall dimensions and the size and number of individual components.

SUMMARY OF THE INVENTION

The disadvantages and limitations of the prior art physical activity sensors described above are overcome by the present invention. With this invention, an improved physical activity sensor for use with a rate-responsive implantable stimulation device (I.S.D.) is provided, which is extremely compact, resistant to fracturing during fabrication and in use, capable of providing a strong output signal, and manufacturable in an efficient, cost-effective manner.

In a preferred embodiment, the sensor is constructed as a cantilever beam having a film of a piezoelectric polymer adhered to each surface of an electrically conductive substrate. The sensor is suitably mounted within the implantable stimulation device so as to be responsive to bodily accelerations associated with physical activity. The accelerations experienced by the sensor cause a free end of the cantilever beam to deflect, which results in measurable electrical potentials appearing across the surfaces of the beam. The induced electrical potentials are indicative of the levels to which the patient is engaged physical activity.

The use of a piezoelectric polymer in the physical activity sensor of the present invention offers several advantages over other known transducing materials, especially piezoelectric crystals. The piezoelectric polymer used as described herein is extremely resilient, which facilitates the fabrication process and improves performance in the field. During fabrication of the physical activity sensor of the present invention, and during installation of the sensor within an implantable stimulation device, the resiliency of the piezoelectric polymer reduces the likelihood of fracturing during handling. Thus, manufacturing procedures may be performed in a more efficient, cost-effective manner.

In the field, the physical activity sensor of the present invention provides a comparatively strong output signal because the sensor is designed to experience stresses of greater magnitude than other known sensors, owing to the resiliency of the piezoelectric polymer. As is known in the art, the magnitude of the output signal from a sensor that uses a piezoelectric material varies in accordance with the magnitude of the stresses experienced by the material. Since the piezoelectric polymer is more resilient than, for example, a piezoelectric crystal, the sensor may be designed so that the polymer is stressed to a greater extent, and accordingly, the output signal provided is much stronger. To illustrate, the sensor of the present invention provides output of about 1 volt/G, whereas some known sensors that use piezoelectric crystals provide output on the order of about 10 millivolts/G.

The physical activity sensor of the present invention also provides an improved supporting structure for anchoring the sensor to a substrate within the implantable stimulation device. Preferably, the substrate upon which the sensor is mounted is the implantable stimulation device hybrid. The supporting structure of the present invention includes a pair of electrically conductive supports which serve to mechanically secure one end of the cantilever beam, and are also operative to conduct the electrical potentials measured across the surfaces of the cantilever beam to circuitry in the implantable stimulation device. In a preferred embodiment, the electrically conductive supports are adhered to conductive traces on the implantable stimulation device hybrid. The supporting structure of the present invention advantageously simplifies the fabrication process and reduces the number of components subject to wear.

The novel supporting structure of the present invention is also designed to enable the sensor to stand freely on a level substrate without the use of an adhesive or a separate mechanical support, such as a shim. In a preferred embodiment, the electrically conductive supports are oriented so that the cantilever beam does not tip toward its free end (which preferably has a mass disposed thereon). This feature is particularly advantageous during the fabrication process, since the epoxies frequently used to secure components to a substrate within an implantable stimulation device are slow-curing, as described above.

In another aspect of the present invention, a method of fabricating the improved physical activity sensor as described above is provided.

The output signal provided by the physical activity sensor of the present invention is conducted to circuitry within a rate-responsive implantable stimulation device, which may be otherwise conventional. The output signal is used by processing circuitry to determine the level to which the patient is engaged in physical activity, and to correlate the determined level of physical activity to a desired heart rate. The processing circuitry causes pulse generating circuitry to maintain the patient's heart rate at the desired rate, preferably by adjusting the escape interval. Pacing pulses are provided by pacing leads, which also may be conventional.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

While the preferred embodiment described below and shown in the figures describes the present invention embodied in the pacemaker, it is understood that this is for illustration purposes only, and that the present invention could be incorporated into any implantable stimulation device which requires a physiologic sensor for rate-responsive pacing.

Figure 1:
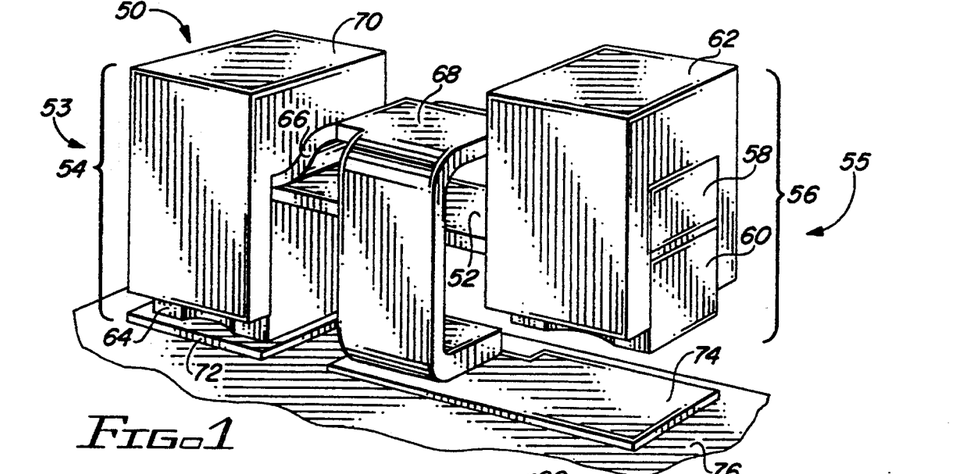
FIG. 1 is a perspective view of a preferred embodiment of a miniature, hybrid-mountable, accelerometer-based, physical activity sensor in accordance with the principles of the present invention.

Referring first to FIG. 1, a preferred embodiment of a miniature, hybrid-mountable, accelerometer-based, physical activity sensor for use with a rate-responsive pacemaker (not shown in FIG. 1) in accordance with the principles of the present invention is described. A sensor 50 as described herein is mounted within the pacemaker so as to be responsive to bodily accelerations associated with physical activity. Preferably, the sensor 50 is mounted so as to be responsive to accelerations along the axis extending from the back to the front of a patient (not shown). It has been experimentally found that accelerations along this axis strongly correlate to the level to which the patient is engaged in physical activity. The sensor 50 provides an output signal to circuitry (not shown in FIG. 1) in the pacemaker, which uses the signal to administer pacing therapy in accordance with measured physical activity.

The embodiment of the sensor 50 shown in FIG. 1 is designed to provide a strong and stable output signal, simplify construction, and minimize the size and the number of components required to construct the sensor 50. As described in detail below, a cantilever beam 52 is the transducing element of the sensor 50. The cantilever beam 52 has a fixed end 53 which is secured by a mount assembly 54, and a free end 55. This design enables the free end 55 of the cantilever beam 52 to deflect in upward and downward directions in response to bodily accelerations, while the fixed end 53 remains secured in place by the mount assembly 54.

The magnitude of the deflections experienced by the free end 55 of the cantilever beam 52 varies in accordance with the magnitude of the bodily accelerations experienced by the sensor 50. However, in a preferred embodiment, a mass assembly 56 is affixed to the free end 55 of the cantilever beam 52 in order to enhance the free end deflections, thereby causing the sensor 50 to provide a stronger output signal. The mass assembly 56 includes a first mass 58 disposed on an upper surface of the cantilever beam 52, a second mass 60 disposed on a lower surface of the cantilever beam 52, and a mass retainer 62 that secures the first and second masses 58 and 60 to the cantilever beam 52. The first and second masses 58 and 60 are preferably made from a dense, non-ferrous material such as platinum, brass, or bronze, or even more preferably, tungsten, and each weighs approximately 13 milligrams. The mass retainer 62 is preferably made from a light plastic material such as acrylonitrile butadiene styrene (ABS), available from GE Plastics Company of Pittsfield, Mass.

Since the first and second masses 58 and 60 are of essentially equal weight, and the weight of the mass retainer 62 is comparatively insignificant, the overall mass assembly 56 is, for practical purposes, symmetrically disposed on the free end 55 of the cantilever beam 52. The sensor 50 is thus substantially nonresponsive to accelerations along the axis parallel to the longer length of the cantilever beam 52, which is advantageous in this design because the sensor 50 can provide a stable output signal despite an occurrence of "twiddler's syndrome," in which the patient absent-mindedly twirls the pacemaker implanted beneath the skin.

As previously mentioned, the cantilever beam 52 is the transducing element of the sensor 50. The novel manner by which the cantilever beam 52 is secured at its fixed end 53 by the mount assembly 54, and by which electrical connections are made between the cantilever beam 52 and the pacemaker, allows the sensor 50 of the present invention to be efficiently constructed using a minimal number of components.

The mount assembly 54 includes a first support 64, a projection 66 extending from a second support 68, and a mount retainer 70. The first support 64, the projection 66, and the second support 68 are electrically conductive, while the mount retainer 70 is made from a light plastic material such as ABS. As shown in FIG. 1, the cantilever beam 52 is inserted between the first support 64 and the projection 66 which extends from the second support 68. The mount retainer 70 urges the projection 66 and the first support 64 against the surfaces of the cantilever beam 52, thereby securing one end of the cantilever beam 52 in place. A suitable epoxy may be used to adhere the components of the mount assembly 54 together.

The second support 68 is interposed between the mount assembly 54 and the mass assembly 56. In a preferred embodiment, the mount assembly 54 and the second support 68 are separated by a length of about 0.024 inches. The second support 68 and the mass assembly 56 are preferably separated by a length of about 0.016 inches. In this configuration, the aforementioned distances are selected with the weight of the mass assembly 56 taken into account, so that the sensor 50 of the present invention is free-standing. More precisely, when the sensor 50 is placed on a level surface with the first and second supports 64 and 68 in contact with the level surface, the sensor 50 stands freely without tipping toward the mass assembly 56. No separate mechanical support, such as a shim or adhesive, is required to prevent the sensor 50 from tipping.

The second support 68 is shaped to permit the cantilever beam 52 to deflect to a sufficient extent so that a relatively strong output signal is 10 provided in response to bodily accelerations associated with physical activity. More particularly, clearances are provided between upper and lower interior surfaces of the second support 68 and the cantilever beam 52, so that the second support 68 does not unduly impede the deflections of the cantilever beam 52.

The embodiment of the sensor 50 shown in FIG. 1 is particularly advantageous with respect to the fabrication process of the pacemaker. In a preferred embodiment, the sensor 50 is intended to be secured with an epoxy (not shown) to a pair of conductive traces 72 and 74 on a suitable substrate 76 within the pacemaker. (As described below, the substrate 76 is preferably the hybrid of the pacemaker.) Epoxies are typically slow-curing adhesives, thus, without the first and second supports 64 and 68 being appropriately spaced as shown, the sensor 50 would tip, unless an additional mechanical support, such as a shim (not shown), was used to restrain the sensor 50 from falling while the epoxy cures.

The embodiment of the sensor 50 shown in FIG. 1 is not only advantageous in the context of mechanical stability during fabrication—it also eliminates the need for separate electrical conductors such as wires, for electrically connecting the surfaces of the cantilever beam 52 to the pacemaker circuitry (not shown). The first and second supports 64 and 68 are electrically conductive, and electrically communicate, respectively, with the lower and upper surfaces of the cantilever beam 52 (the second support 68 communicates with the upper surface of the cantilever beam 52 via the electrically conductive projection 66). The first and second supports 64 and 68 contact, respectively, the conductive traces 72 and 74 that are deposited onto the substrate 76, which in a preferred embodiment, is the hybrid substrate of the pacemaker. The conductive traces 72 and 74 conduct the output signal from the sensor 50 to signal processing circuitry (not shown), and after processing, the output signal may be used by the pacemaker to provide rate-responsive pacing therapy. Thus, the first and second supports 64 and 68 serve not only as mechanical supports, but also as electrical conductors between the sensor 50 and the pacemaker circuitry (not shown), thereby eliminating the need for additional electrical conductors that would otherwise be necessary.

In addition to being designed with a minimal number of components, the sensor 50 may be constructed to be extremely compact, thereby conserving limited space available within the pacemaker. For example, in a preferred embodiment, the length of the sensor 50 extending from the mount assembly 54 to the mass assembly 56 is about 0.150 inches, the height extending from the lower surface of the second support 68 to the upper surface of the mass assembly 56 is about 0.088 inches, and the width of the mount assembly 54 is about 0.094 inches. Thus, the sensor 50 is designed to minimize the amount of space it requires, for example, on a typically crowded hybrid (not shown).

Figure 2:
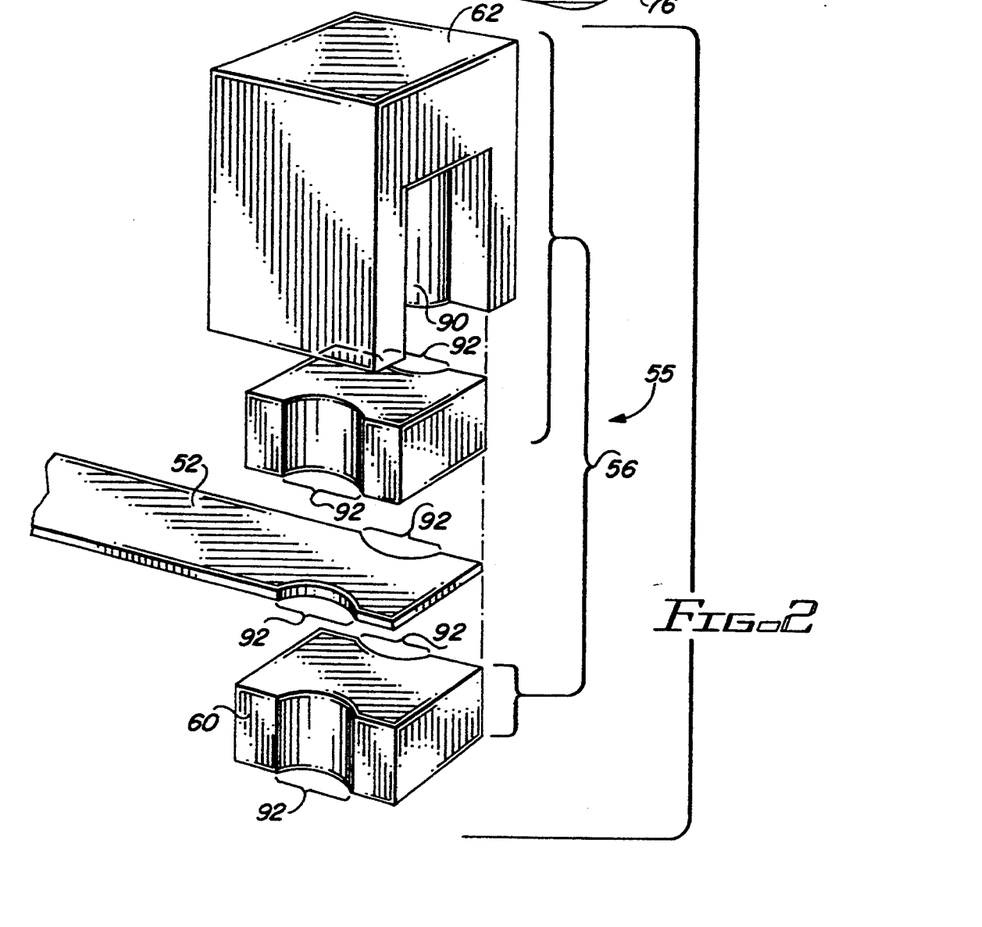
FIG. 2 is an exploded, perspective view of a cantilever beam and mass assembly of the physical activity sensor shown in FIG. 1, depicting an interlocking construction feature in accordance with the principles of the present invention.

Referring now to FIG. 2, a construction feature of the sensor 50 of FIG. 1 is described which improves the safety and reliability of a pacemaker (not shown) using the sensor 50. The free end 55 of the cantilever beam 52, the first and second masses 58 and 60, and the mass retainer 62 are shown as they may appear prior to subassembly of the mass assembly 56. The two interior surfaces of the mass retainer 62 are each shaped to have a protruding radius 90 extending therefrom (only one protruding radius 90 is visible in FIG. 2). The first and second masses 58 and 60 and the free end 55 of the cantilever beam 52 each have a pair of indentations 92 which correspond to the protruding radii 90 of the mass retainer 62. When the components of the mass assembly 56 are secured together, the protruding radii 90 register with the corresponding indentations 92 of the first and second masses 58 and 60 and the cantilever beam 52. This arrangement causes the cantilever beam 52 to be effectively locked into the mass assembly 56, so that if an adhesive (not shown) used to secure the first and second masses 58 and 60 to the cantilever beam 52 unexpectedly fails to hold, the mass assembly 56 remains in place (as long as the adhesive securing the second mass 60 to the mass retainer 62 remains in tact).

Figure 11:
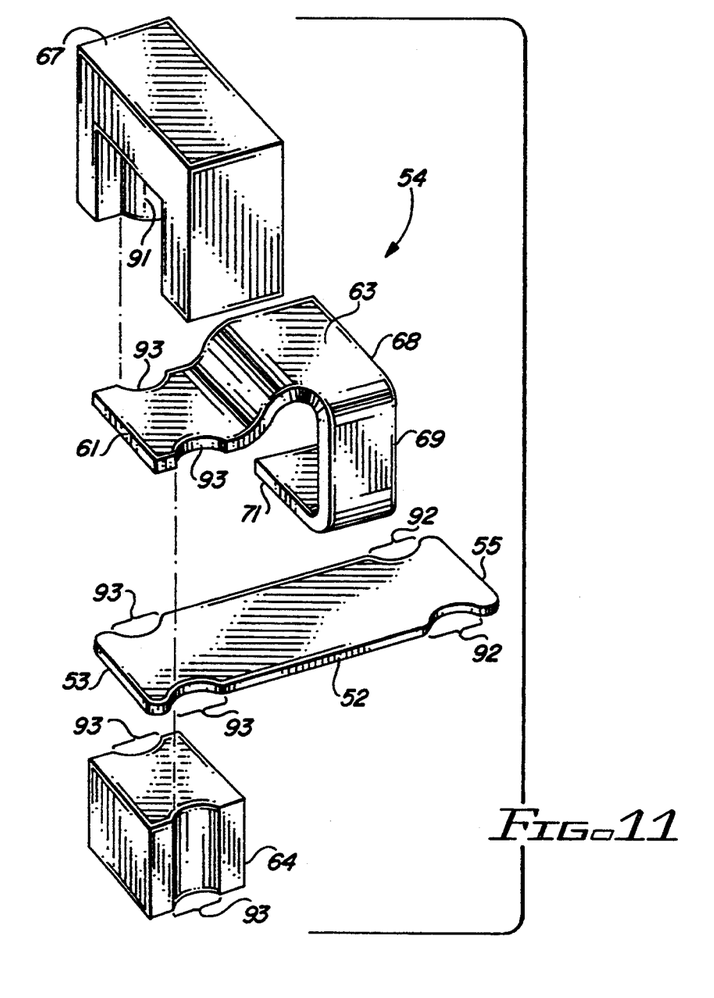
FIG. 11 is an exploded, perspective view of an arrangement for securing the fixed end of the cantilever beam with the mount assembly shown in FIG. 1.

A similar arrangement, shown in FIG. 11, is used to secure the fixed end 53 of the cantilever beam 52 within the mount assembly 54 shown in FIG. 1. Referring now to FIG. 11, a construction of the fixed end 53 is described, which improves the safety and reliability of the pacemaker (not shown), using sensor 50. The fixed end 53 of the cantilever beam 52, the first and second supports 64 and 68, and the nonconductive mount retainer 67 are shown in an exploded view. The two interior surfaces of the nonconductive mount retainer 67 are each shaped to have a protruding radius 91 extending therefrom. (Only one protruding radius 91 is visible in FIG. 11.) The first and second supports 64 and 68 have a pair of indentations 93, which correspond to the protruding radii 91 of the nonconductive mount 67. During assembly, the conductive beam 52 is inserted between the first support 64 and a flat portion 61 of the second support 68. The second support 68 further has a top portion 63, a leg portion 69, and a foot portion 71. Each of the top, foot and leg portions 63, 69 and 71 of the second support 68 are shaped so that the free end 55 of the cantilever beam 52 does not restrict the deflections caused by bodily accelerations seen during operation. The foot portion 71 is designed to make contact directly to a first contact pad on a hybrid substrate. The first support 64 also is designed to make electrical contact with a second contact pad on a hybrid substrate. During assembly, the fixed end 53 of the cantilever beam 52 is inserted between the first support 64 and the flat portion 61 of the second support 68. When the first and second supports 64 and 68 are aligned with the indentations 92 of the cantilever beam 52, the protruding radii 91 of the nonconductive mount 67 will register with the corresponding indentations 93 of the first and second supports 64 and 68 and the cantilever beam 52. This arrangement causes the cantilever beam 52 to be effectively locked into the nonconductive mount retainer 67 so that, if an adhesive (not shown) unexpectedly fails to hold the first and second supports 64 and 68 to the cantilever beam 52, the nonconductive mount 67 remains in place. The interlocking construction of the present invention improves safety and reliability, because the possibility of an output signal interruption or reduction resulting from unexpected slippage of the cantilever beam 52 is substantially reduced.

Figure 3:
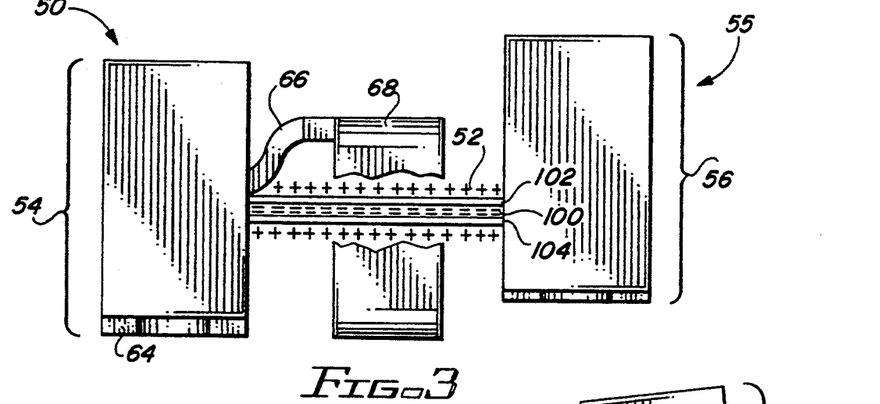
FIG. 3 is a partial side view of the physical activity sensor shown in FIG. 1, depicting a cantilever beam of the physical activity sensor in a resting state.
Figure 4:
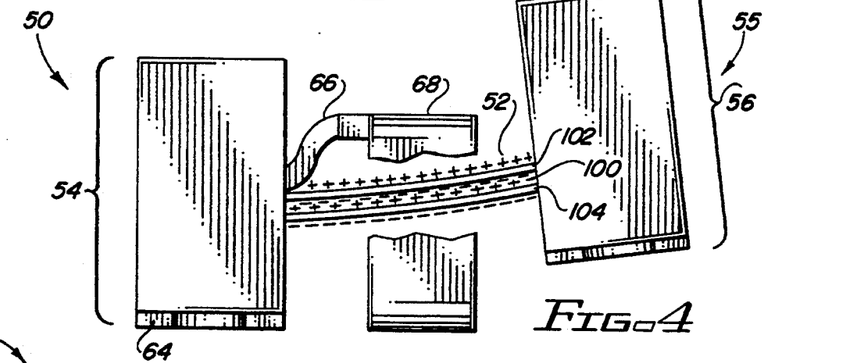
FIG. 4 is another partial side view of the physical activity sensor shown in FIG. 1, depicting an induced potential across a cantilever beam of the physical activity sensor resulting from an upward deflection of the cantilever beam.
Figure 5:
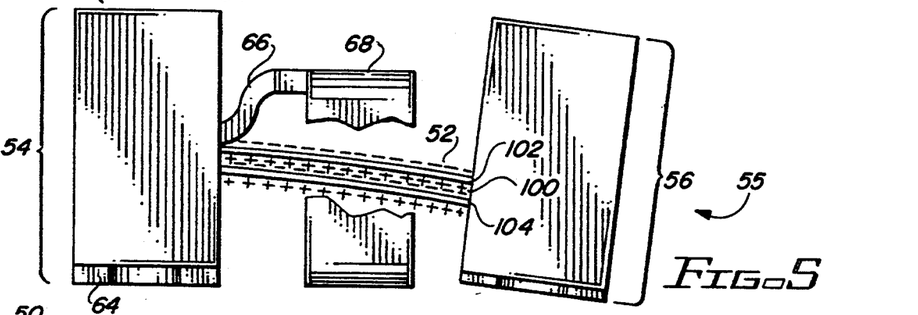
FIG. 5 is another partial side view of the physical activity sensor shown in FIG. 1, depicting an induced potential across a cantilever beam of the physical activity sensor resulting from a downward deflection of the cantilever beam.

Referring collectively to FIGS. 3–5, a preferred embodiment of the cantilever beam 52 suitable for use as the transducing element for the sensor 50 in accordance with the principles of the present invention is described. In order to provide an output signal representative of bodily accelerations, the cantilever beam 52 incorporates a material having an electrical characteristic that varies measurably in response to mechanical stresses experienced by the cantilever beam 52. The mechanical stresses are the result of conformational changes (i.e., upward and downward deflections) caused by bodily accelerations associated with physical activity.

In the preferred embodiment shown in FIGS. 3–5, the cantilever beam 52 is constructed from a beam substrate 100 having a first transducing layer 102 laminated to its upper surface and a second transducing layer 104 laminated to its lower surface. The first transducing layer 102 is adhered such that it will make electrical contact with the projection 66 extending from the second support 68, and the second transducing layer 104 is adhered such that it will make electrical contact with the first support 64 of the mount assembly 54. The beam substrate 100 is formed from an electrically conductive metal, preferably one of low ductility such as titanium or beryllium. Low ductility is desirable so that the cantilever beam 52 does not "creep," i.e., ultimately conform or permanently bend as a result of the load created by the mass assembly 56. The first and second transducing layers 102 and 104 are preferably films of a piezoelectric polymer, such as polyvinylidene fluoride (commonly known by the trademark KYNAR, owned by ATOCHEM North America). When a piezoelectric polymer is used on the cantilever beam 52, electrical potentials are generated between the upper and lower surfaces of the cantilever beam 52 when the cantilever beam 52 experiences mechanical stresses.

Although in the preferred embodiment the cantilever beam 52 is constructed as a piezoelectric bimorph with a beam substrate 100, other configurations are possible. For example, the cantilever beam 52 may be constructed with a piezoelectric film on only one surface of the beam substrate 100, thereby forming a piezoelectric monomorph (not shown). Alternatively, the cantilever beam 52 may be constructed as a piezoelectric bimorph in which two piezoelectric films are adhered to one another and are not separated by a beam substrate (not shown).

The use of a piezoelectric polymer in accordance with the principles of the present invention offers several advantages as compared to materials used in other physical activity sensors known in the art. For example, the first and second transducing layers 102 and 104 made from a piezoelectric polymer are extremely resilient as compared to piezoelectric crystals, and are thus less likely to fracture during fabrication and in use. Also, the resiliency of the first and second transducing layers 102 and 104 advantageously enables the cantilever beam 52 to deflect to a much greater extent than sensors which use piezoelectric crystals. Thus, the sensor 50 of the present invention is capable of providing output of about 1 volt/G, while many prior art physical activity sensors are limited to providing output of up to about 10 millivolts/G.

FIG. 3 depicts the cantilever beam 52 as it appears during a resting state of the sensor 50 (no motion). During construction of the cantilever beam 52, the first and second transducing layers 102 and 104 are polarized such that one surface of each layer has a positive charge and the other surface of each layer has a negative charge. As shown in FIG. 3, the first and second transducing layers 102 and 104 are adhered to the beam substrate 100 such that each negatively charged surface makes contact with the beam substrate 100. Thus, in the resting state of the sensor 50, there is no potential difference between the first support 64 and the second support 68.

FIG. 4 shows a change in polarization of the second transducing layer 104 during an upward deflection of the free end 55 of the cantilever beam 52, caused by an acceleration experienced by the sensor 50. As the second transducing layer 104 is bent upward, the polarization of the second transducing layer 104 inverts, causing a negative charge to appear on the lower surface of the cantilever beam 52, while the first transducing layer 102 retains a positive charge on its upper surface. Thus, an overall positive potential is measurable between the first support 64 and the second support 68. The magnitude of the positive potential varies in accordance with the magnitude of the upward deflection of the free end 55 of the cantilever beam 52.

FIG. 5 shows a change in polarization of the first transducing layer 102 during a downward deflection of the free end 55 of the cantilever beam 52. As the first transducing layer 102 is bent downward, the polarization of the first transducing layer 102 inverts, causing a negative charge to appear on the upper surface of the cantilever beam 52, while the second transducing layer 104 retains a positive charge on its lower surface. Thus, an overall negative potential is measurable between the first support 64 and the second support 68. In a similar manner as described for a positive potential resulting from an upward deflection, the magnitude of the negative potential varies in accordance with the magnitude of the downward deflection of the free end 55 of the cantilever beam 52.

Figure 6:
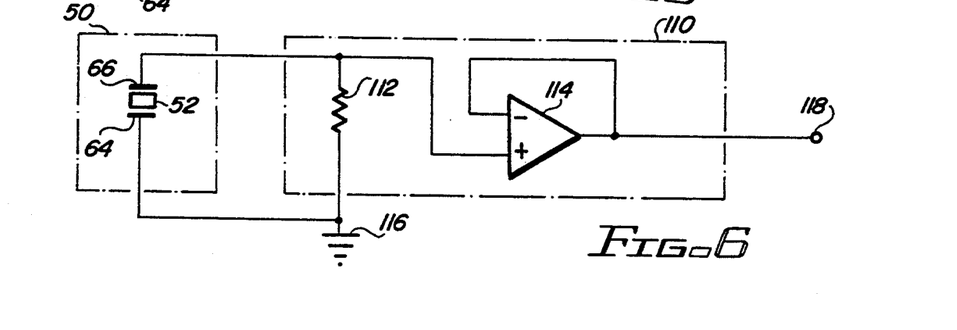
FIG. 6 is a schematic diagram of signal processing electronics used to initially process the raw signal provided by the physical activity sensor shown in FIG. 1 in accordance with the principles of the present invention.

Referring now to FIG. 6, an electronic circuit is shown for initially processing the output signal provided by the preferred embodiment of the physical activity sensor 50 described with respect to FIGS. 1-5. A processing circuit 110 is preferably included on the hybrid (not shown) of the pacemaker (not shown). In FIG. 6, the sensor 50 is schematically illustrated as including only the cantilever beam 52, the projection 66, and the first support 64. It should be understood that the raw output signal being initially processed by the processing circuit 110 is the varying potential that appears across the cantilever beam 52 in the manner described with respect to FIGS. 3-5.

In the preferred embodiment, the projection 66 (which contacts the upper surface of the cantilever beam 52) is connected to one end of a resistor 112 and also to the noninverting input of an operational amplifier 114 (via the second support 68 shown in FIGS. 1-5). The first support 64 (which contacts the lower surface of the cantilever beam 52) and the other end of the resistor 112 are connected to a ground node 116. The output from the operational amplifier 114 is fed back to its inverting input. The operational amplifier 114 is, of course, an active element, and is supplied with power from a power supply (not shown) within the pacemaker. The resistor 112 has a high value of resistance, preferably about 22 gigohms, so that the processing circuit 110 serves as a filter that limits the output from the processing circuit 110 taken at an output terminal 118 to frequency components associated with bodily accelerations. The signal at the output terminal 118 is provided to other circuitry (not shown) in the pacemaker for correlating physical activity to heart rate.

Figure 7:
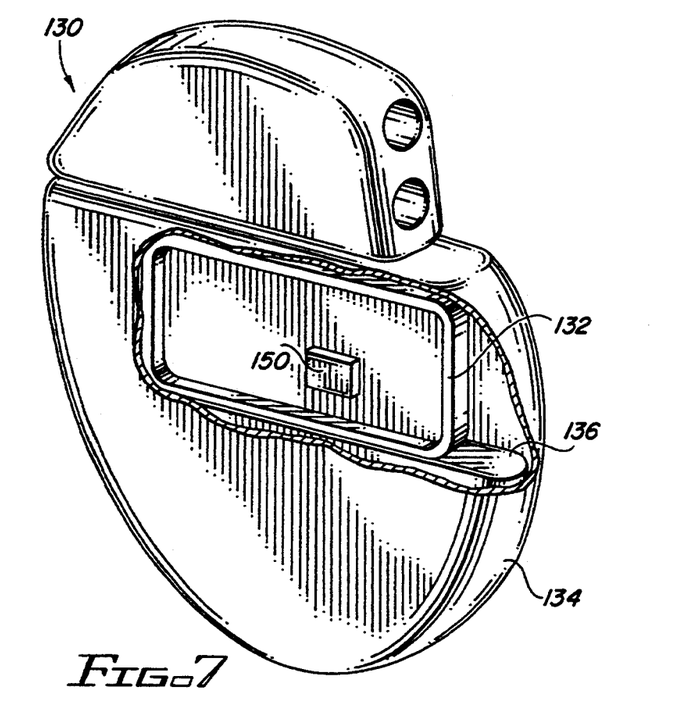
FIG. 7 is a partial cutaway view of a rate-responsive implantable stimulation device having the physical activity sensor shown in FIG. 1 mounted to a hybrid in accordance with the principles of the present invention.

Referring now to FIG. 7, a portion of the interior of a pacemaker is shown to illustrate a preferred mounting location for a physical activity sensor in accordance with the principles of the present invention. In FIG. 7, a pacemaker 130 is shown having a hybrid 132 disposed within an implantable housing 134. A battery 136 is disposed within the lower portion of the implantable housing 134. The pacemaker 130 may include other components, but they are not pertinent in the present context.

The hybrid 132 supports circuitry (not shown) which allows the pacemaker to provide rate-responsive pacing therapy to a patient (not shown). In this preferred embodiment, a sensor 150 (schematically depicted as a block in FIG. 7 and not drawn to scale) is bonded to a surface of the hybrid 132. The sensor 150 is constructed in a manner substantially as described with respect to FIGS. 1-5. In this configuration, the hybrid 132 serves the purpose described for the substrate 76 of FIG. 1. The hybrid 132 has conductive traces deposited thereon (not shown, but similar to the conductive traces 72 and 74 of FIG. 1), and the sensor 150 has first and second supports (not shown, but similar to the first and second supports 64 and 68 of FIG. 1) which contact the conductive traces (the connections are hidden from view in FIG. 7, but are similar to the connections shown in FIG. 1). Mounting the sensor 150 to the hybrid 132 is advantageous, because assembly and installation of the sensor 150 may be incorporated into the fabrication process of the hybrid 132.

Figure 8:
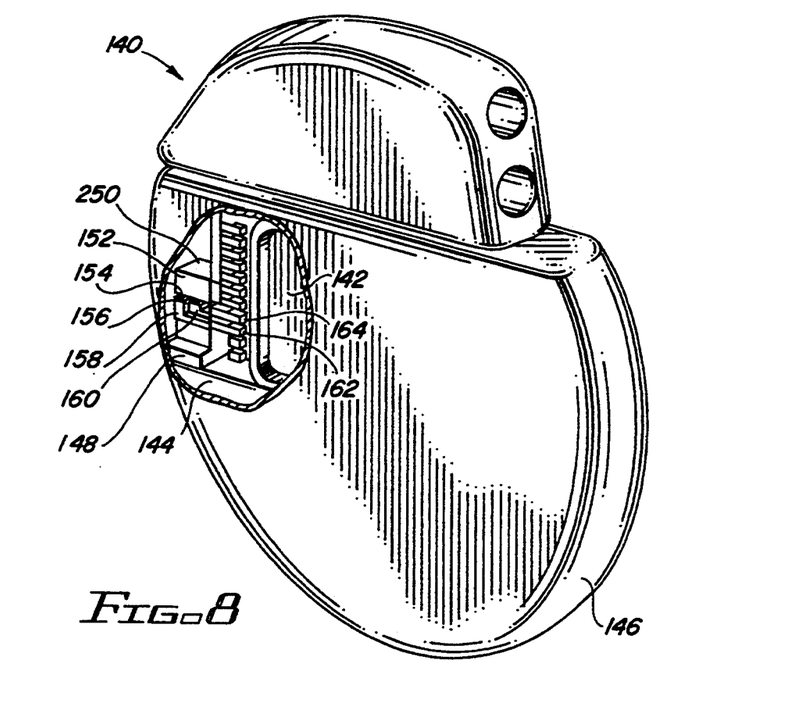
FIG. 8 is a partial cutaway view of a rate-responsive implantable stimulation device having the physical activity sensor shown in FIG. 1 disposed within a battery support in accordance with the principles of the present invention.

An alternative mounting location for the physical activity sensor of the present invention is shown in FIG. 8. To illustrate this embodiment, a pacemaker 140 is shown having a hybrid 142 and a battery 144 disposed within an implantable housing 146. The pacemaker 140 also includes a battery support 148 which is adhered to the interior of the pacemaker 140 and serves to secure the battery 144.

The battery support 148 includes a cavity which contains a sensor 250 constructed in a manner substantially as described with respect to FIGS. 1-5. A substrate 152, upon which the sensor 250 is mounted, has two electrically conductive conduits (not shown) for electrically connecting first and second supports (not shown, but similar to the first and second supports 64 and 68 described with respect to FIG. 1) to a pair of conductive pads 154 and 156 adhered to the exterior surface of the substrate 152. A pair of wires 158 and 160 are used to connect the conductive pads 154 and 156 to a pair of terminals 162 and 164 on the hybrid 142. Circuitry (not shown) on the hybrid 142 is thereby provided with the output signal from the sensor 250, which may be subsequently processed and used by the pacemaker 140 to provide rate-responsive pacing therapy.

Figure 9:
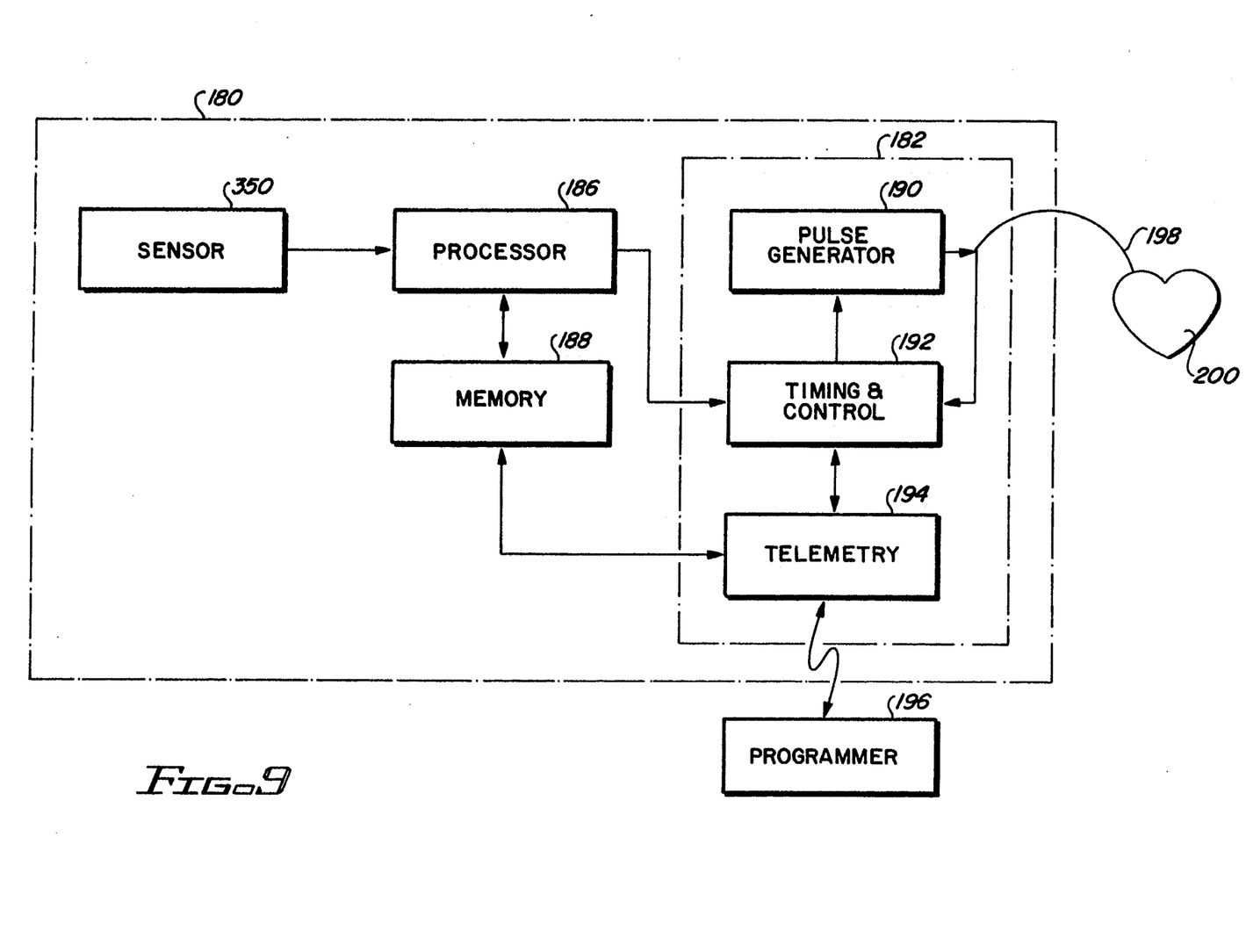
FIG. 9 is a schematic block diagram of a rate-responsive implantable stimulation device including a physical activity sensor in accordance with the principles of the present invention.

Referring now to FIG. 9, a block diagram illustrating the operation of a pacemaker that uses a signal representative of physical activity provided by a physical activity sensor in accordance with the principles of the present invention is described. A pacemaker 180 includes a conventional pacemaker circuit 182, a physical activity sensor 350 (such as the sensor 50 described with respect to FIGS. 1-5), a processor 186 coupled to the sensor 350, and a memory circuit 188 coupled to processor 186. The pacemaker circuit includes a pulse generator circuit 190, a timing and control circuit 192 coupled to the pulse generator circuit 190 and to the processor 186, and a telemetry circuit 194. The telemetry circuit 194 telemetrically communicates with an external programmer 196, and is coupled within the pacemaker 180 to the memory circuit 188 and the timing and control circuit 192.

Coupled to the pulse generator circuit 190 is at least one conventional pacing lead 198. The pacing lead 198 is used to deliver pacing pulses provided by the pulse generator circuit 190 to a patient's heart 200. In addition, the pacing lead 198 senses intrinsic activity of the heart 200, and presents a signal indicative thereof to the timing and control circuit 192. Thus, the pacemaker 180 is capable of operating in a "demand mode," in which delivery of a pacing pulse is inhibited by the timing and control circuit 192 when an intrinsic cardiac contraction is sensed during the escape interval following a preceding contraction.

Although the following description assumes that the pacemaker 180 is operating in a demand mode, it should be understood that a simpler implementation is possible, in which the pacemaker 180 does not inhibit delivery of pacing pulses when intrinsic contractions are sensed. Also, a demand mode may be a telemetrically programmable feature, allowing the pacemaker to be switched into and out of demand mode when desired by a physician.

In operation, the sensor 350 responds to bodily accelerations associated with physical activity. A sensor signal is generated by the sensor 350, which is indicative of the level to which the patient is engaged in physical activity. For the purposes of this discussion, the processing circuit 110 described with respect to FIG. 6 is assumed to be incorporated within the sensor 350, although other arrangements are possible. The sensor signal is provided to the processor 186, which further processes the sensor signal using conventional techniques (e.g., averaging, half-wave rectification, full-wave rectification) to determine a current level of physical activity. The processor 186 in turn provides a rate control signal to the timing and control circuit 192, which determines the heart rate to be maintained by the pacemaker 180. In a preferred embodiment, the rate control signal provided by the processor 186 adjusts the escape interval used by the timing and control circuit 192, which has the effect of increasing or decreasing the maintained heart rate. It should be noted that the pacemaker 180 can also be telemetrically programmed by the programmer 196 to operate in a constant rate mode if desired by the physician.

Figure 10:
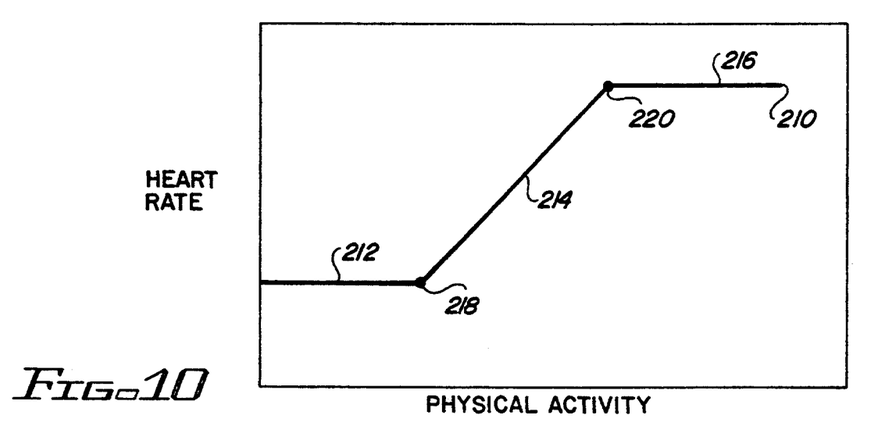
FIG. 10 depicts a representative transfer curve used by a rate-responsive implantable stimulation device in accordance with the principles of the present invention.

The manner by which the pacemaker 180 adjusts the maintained heart rate in accordance with a signal provided by the sensor 350 of the present invention may be understood by reference to a transfer curve shown in FIG. 10. A transfer curve 210 correlates physical activity (as measured by the sensor 350 of FIG. 9) along the horizontal axis with a desired heart rate along the vertical axis. The transfer curve 210 has three segments—a minimum rate segment 212, a slope segment 214, and a maximum rate segment 216, each of which may be telemetrically varied to meet the needs of a particular patient. For example, a physician may set the minimum rate segment 212 at 60 beats per minute, and may set a first activity threshold 218 at a relatively low level of physical activity that is required before the pacemaker 180 (FIG. 9) abandons the heart rate defined by the minimum rate segment 212 in favor of a heart rate determined by the slope segment 214. The physician may set the maximum rate segment 216 at, for example, 120 beats per minute, and may set a second activity threshold 220 at a relatively high level of physical activity that is required before the pacemaker 180 (FIG. 9) discontinues using the slope segment 214 in favor of the heart rate corresponding to the maximum rate segment 216. In addition, the slope segment 214 may be telemetrically adjustable, so that changes to the maintained heart rate may be more gradual or more aggressive, depending upon the needs of a particular patient.

Information defining the transfer curve 210 is stored in the memory 188 (FIG. 9) of the pacemaker 180 (FIG. 9) in a conventional manner. For example, the transfer curve 210 may be stored as a collection of discrete data points in a look-up table. Alternatively, the minimum rate segment 212 and the maximum rate segment 216 may be stored discretely, and the slope segment 214 may be stored as a mathematical algorithm which is used by the processor 186 (FIG. 9) to compute the appropriate heart rate to be maintained when the determined level of physical activity as measured by the sensor 350 (FIG. 9) falls between the first activity threshold 218 and the second activity threshold 220.

Thus a miniature, hybrid-mountable, accelerometer-based, physical activity sensor for use with a rate-responsive pacemaker is provided. One skilled in the art will appreciate that the present invention can be practiced by other than the described embodiments, which are presented for purposes of illustration and not of limitation, and the present invention is limited only by the claims which follow.

What is claimed is:

1. An accelerometer for providing a signal indicative of bodily accelerations associated with physical activity to circuitry in an implantable cardiac stimulating device, the accelerometer comprising:
   transducing element means for generating a signal in accordance with mechanical stresses resulting from deflections of the free end of the transducing element caused by the bodily accelerations, wherein the transducing element means comprises:
   a cantilever beam having a fixed end and a free end and including a material having an electrical characteristic that varies measurably when the cantilever beam experiences mechanical stresses; and
   supporting means for securing the fixed end and for enabling the free end to deflect in response to the bodily accelerations, the supporting means having means for preventing the accelerometer from tipping toward the free end of the transducing element when the accelerometer rests unsecured, wherein the supporting means comprises:
   a first electrically conductive support member in contact with a first surface of the cantilever beam at the fixed end; and
   a second electrically conductive support member substantially interposed between the first support member and the free end, the second support member having means for supporting the free end without restricting the deflections caused by the bodily accelerations.

2. The accelerometer of claim 1, wherein the second support member comprises:
   an electrically conductive projection which contacts a second surface of the cantilever beam at the fixed end.

3. The accelerometer of claim 1, wherein the supporting means further comprises:
   nonconductive mount retainer means for interlocking the cantilever beam with the first support member and the projection for preventing slippage of the cantilever beam from the supporting means.

4. The accelerometer of claim 3, wherein:
   the nonconductive mount retainer means includes a housing having protruding radii and the cantilever beam, first and second support members each include regions defining indentations which conform in shape to the protruding radii, whereby the protruding radii of the nonconductive mount retainer means register with the indentations of the cantilever beam and first and second support members when the nonconductive mount retainer means is disposed on the fixed end.

5. The accelerometer of claim 1, wherein the material comprises:
   a first film of a piezoelectric polymer that causes an electrical potential to appear across first and second surfaces of the cantilever beam.

6. The accelerometer of claim 5, wherein the cantilever beam comprises:
   an electrically conductive beam substrate, and the first film is electrically connected to a first surface of the beam substrate.

7. The accelerometer of claim 6, wherein the cantilever beam further comprises:
   a second film of the piezoelectric polymer electrically connected to a second surface of the beam substrate, whereby the first and second films are connected in series.

8. An accelerometer for providing a signal indicative of bodily accelerations associated with physical activity to circuitry in an implantable cardiac stimulating device, the accelerometer comprising:

transducing means for generating a signal in accordance with mechanical stresses caused by bodily accelerations, wherein the transducing means comprises a cantilever beam having a fixed end and a free end, the cantilever beam including a material having an electrical characteristic that varies measurably when the cantilever beam experiences mechanical stresses; and a mass assembly disposed on the free end, which enhances the mechanical stresses experienced by the cantilever beam, wherein the mass assembly includes means for interlocking the mass assembly with the cantilever beam to prevent slippage of the cantilever beam from the mass assembly, wherein the mass assembly comprises nonconductive mass retainer means having protruding radii and a mass having regions defining indentations which conform in shape to the protruding radii; and the cantilever beam comprises regions defining indentations which also conform in shape to the protruding radii, whereby the protruding radii of the mass retainer register with the indentations of the mass and with the indentations of the cantilever beam when the mass assembly is disposed on the free end; and supporting means for securing the fixed end and for enabling the free end to deflect in response to bodily accelerations, the supporting means having means for preventing the accelerometer from tipping toward the free end of the transducing element when the accelerometer rests unsecured.

9. An accelerometer-based physical activity sensor suitable for use in a rate-responsive implantable stimulation device, the sensor comprising:

a cantilever beam having a fixed end and a free end, and including a piezoelectric polymer which causes electrical potentials to appear across first and second surfaces of the cantilever beam when the cantilever beam experiences mechanical stresses caused by bodily accelerations;

a first electrically conductive support member in contact with the first surface of the cantilever beam at the fixed end; and a second electrically conductive support member substantially interposed between the first support member and the free end, the second support member being positioned with respect to the first support member and the free end of the cantilever beam so as to prevent the sensor from tipping toward the free end of the cantilever beam when the sensor rests unsecured.

10. The sensor of claim 9, wherein the cantilever beam comprises:

an electrically conductive beam substrate; and a first film of the piezoelectric polymer is electrically connected to a first surface of the beam substrate.

11. The sensor of claim 10, wherein the cantilever beam further comprises:

a second film of the piezoelectric polymer electrically connected to a second surface of the beam substrate;

whereby the first and second films of piezoelectric polymer are connected in series.

12. The sensor of claim 9, wherein the first and second electrically conductive support members include:

means for electrically connecting the first and second surfaces of the cantilever beam to conduct the electrical potentials to circuitry within the implantable stimulation device through the first and second contact pads, respectively, of the hybrid substrate.

13. The sensor of claim 12, wherein the second support member includes:

an electrically conductive projection which contacts the second surface of the cantilever beam at the fixed end.

14. The sensor of claim 13, wherein the supporting structure comprises:

nonconductive mount retainer means for interlocking the cantilever beam with the first support member and the projection to prevent slippage of the cantilever beam from the supporting structure.

15. The sensor of claim 14, wherein:

the nonconductive mount retainer includes a housing having protruding radii; and the cantilever beam, the first and second support members includes regions defining indentations which conform in shape to the protruding radii;

whereby the protruding radii of the nonconductive mount retainer register with the indentations of the cantilever beam, the first and second support members when the nonconductive mount retainer is disposed on the fixed end.

16. The sensor of claim 9, further comprising:

a mass assembly disposed on the free end of the cantilever beam for enhancing the mechanical stresses experienced by the cantilever beam, wherein the mass assembly includes means for interlocking the mass assembly with the cantilever beam to prevent slippage of the cantilever beam from the mass assembly.

17. The sensor of claim 16, wherein:

the mass assembly comprises a mass retainer having protruding radii and a mass having regions defining indentations which conform in shape to the protruding radii; and the cantilever beam comprises regions defining indentations which also conform in shape to the protruding radii;

whereby the protruding radii of the mass retainer register with the indentations of the mass and with the indentations of the cantilever beam when the mass assembly is disposed on the free end of the cantilever beam.

18. A method of fabricating a physical activity sensor for use with a rate-responsive implantable stimulation device, comprising the steps of:

forming a cantilever beam incorporating a material having an electrical characteristic that varies measurably when the transducing element experiences mechanical stresses in response to bodily accelerations associated with physical activity;

securing a first end of the cantilever beam between a first electrically conductive support member of a support structure and an electrically conductive projection extending from a second electrically conductive support member of the support structure; and interposing the second support member between the first support member and a second end of the cantilever beam to permit the second end to deflect in response to the bodily accelerations and to prevent the sensor from tipping toward the second end when the sensor rests unsecured on a microelectronic substrate.

19. The method of claim 18, wherein the forming step further comprises the steps of:
    providing an electrically conductive beam substrate; and
    adhering a first film of piezoelectric polymer to a first surface of the beam substrate.

20. The method of claim 19, wherein the forming step further comprises the step of:
    adhering a second film of piezoelectric polymer to a second surface of the beam substrate so that the first and second film of piezoelectric polymer are electrically connected in series through the conductive beam.

21. The method of claim 22, further comprising the step of:
    interlocking the first end of the cantilever beam with the first support member and the projection using a nonconductive mount retainer to prevent the cantilever beam from slipping from the support structure.

22. The method of claim 22, further comprising the step of:
    interlocking a symmetrical mass assembly to a second end of the cantilever beam to enhance the mechanical stresses experienced by the cantilever beam.

23. The method of claim 22, wherein the interlocking step comprises the steps of:
    providing indentations in a mass;
    providing indentations in the cantilever beam; and
    attaching the mass to the second end of the cantilever beam using a nonconductive mass retainer having protruding radii which register with indentations in the mass and the cantilever beam.

24. A body motion detecting accelerometer for mounting on a desired flat surface in a pacemaker, the accelerometer comprising:
    first and second supports for supporting the accelerometer on the desired flat surface;
    a cantilever beam having a fixed end and a free end, the fixed end being secured to the first support, the beam comprising beam material having first and second sides, such sides having electrical characteristics that vary as a function of mechanical stresses induced in the beam material caused by deflections of the beam, said first support being electrically coupled to the first side of the beam material, the first support having a support portion for contact with the desired flat surface, said second support being mechanically coupled to the first support and electrically coupled to the second side of the beam material, the second support having a support portion depending from the first support for contact with the desired flat surface; and
    a mass coupled to the free end of the cantilever beam, the beam material being of sufficient rigidity to maintain the mass freely suspended, the beam material deflecting under the load created by the mass resulting from bodily accelerations associated with physical activity.

* * * * *